(12) United States Patent
Aoki et al.

(10) Patent No.: US 10,485,493 B2
(45) Date of Patent: Nov. 26, 2019

(54) MEDICAL IMAGE DIAGNOSIS SYSTEM

(71) Applicant: Canon Medical Systems Corporation, Otawara-shi (JP)

(72) Inventors: Kohei Aoki, Nasushiobara (JP); Shigeru Usuda, Otawara (JP); Yoshihito Abe, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 115 days.

(21) Appl. No.: 15/900,960

(22) Filed: Feb. 21, 2018

(65) Prior Publication Data

US 2018/0235552 A1 Aug. 23, 2018

(30) Foreign Application Priority Data

Feb. 22, 2017 (JP) .................................. 2017-030842

(51) Int. Cl.
*A61B 6/00* (2006.01)
*A61B 6/03* (2006.01)
*G01N 23/046* (2018.01)

(52) U.S. Cl.
CPC .............. *A61B 6/035* (2013.01); *A61B 6/032* (2013.01); *A61B 6/037* (2013.01); *A61B 6/4405* (2013.01); *A61B 6/4423* (2013.01); *A61B 6/4429* (2013.01); *A61B 6/54* (2013.01); *G01N 23/046* (2013.01); *G01N 2223/419* (2013.01)

(58) Field of Classification Search
CPC ..... A61B 6/035; A61B 6/4405; A61B 6/4423; A61B 6/4429; A61B 6/54; A61B 6/032; A61B 6/037; G01N 23/046; G01N 23/419; G01N 2223/419
See application file for complete search history.

(56) References Cited

U.S. PATENT DOCUMENTS 4,645,933 A * 2/1987 Gambini .............. A61B 6/4405
250/363.05
2015/0320376 A1* 11/2015 Oishi ................... A61B 6/4405
378/199

FOREIGN PATENT DOCUMENTS

JP 2015-058045 3/2015

* cited by examiner

*Primary Examiner* — Kiho Kim
(74) *Attorney, Agent, or Firm* — Oblon, McClelland, Maier & Neustadt, L.L.P.

(57) ABSTRACT

According to one embodiment, a medical image diagnosis system includes a gantry, a rail, an absorbing member and a carrier unit. The rail is disposed on a floor. The rail cover covers the rail. The absorbing member is formed between the floor and the rail cover. The carrier unit is formed in a bottom of the gantry, and is moved along the rail through a space between the rail and the rail cover, and along with movement, attaches and detaches the rail cover with respect to the floor via the absorbing member.

11 Claims, 11 Drawing Sheets

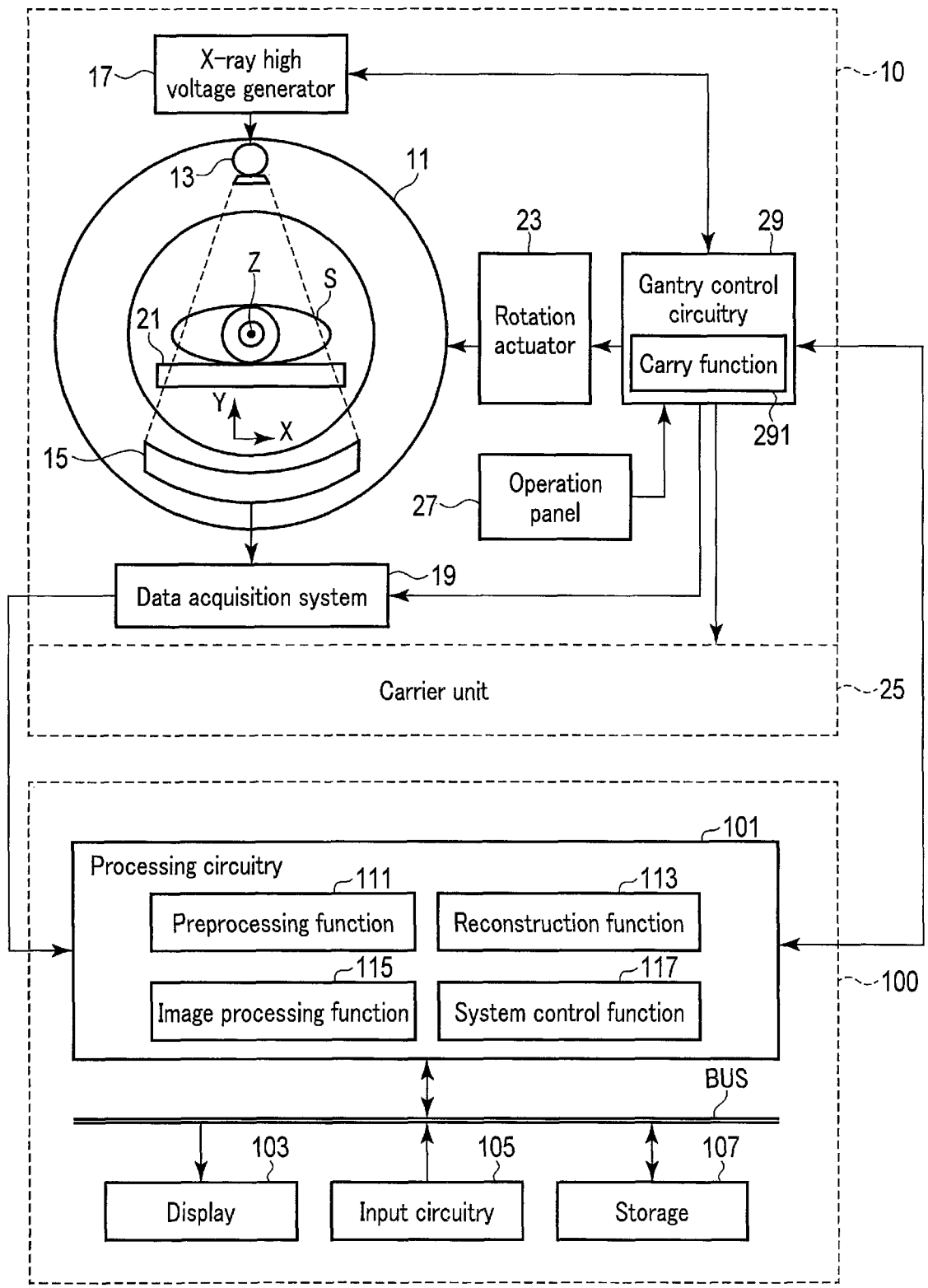
F I G. 2

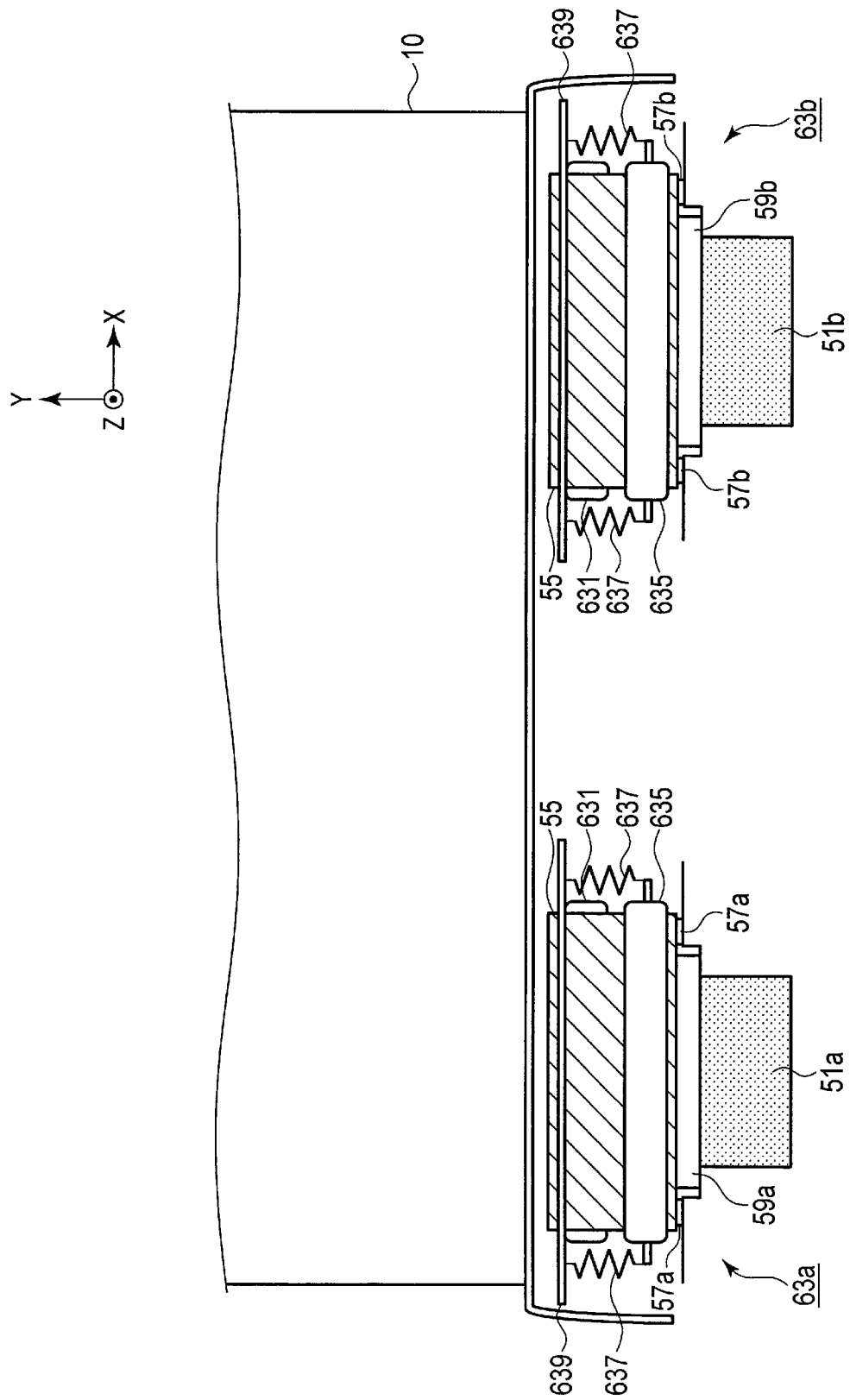
F I G. 10

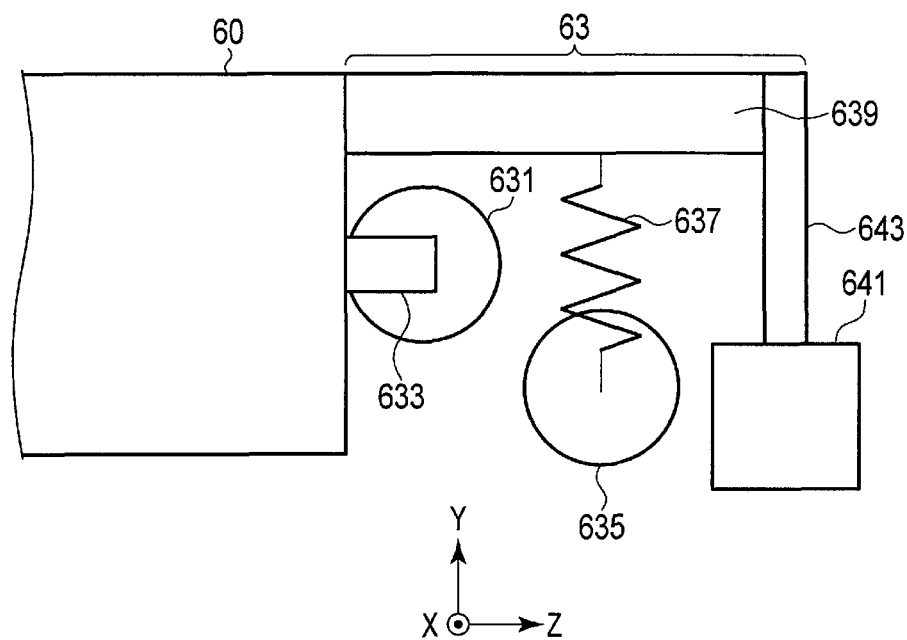
F I G. 14

MEDICAL IMAGE DIAGNOSIS SYSTEM

CROSS-REFERENCE TO RELATED APPLICATIONS

This application is based upon and claims the benefit of priority from the prior Japanese Patent Application No. 2017-030842, filed Feb. 22, 2017, the entire contents of all of which are incorporated herein by reference.

FIELD

Embodiments described herein relate generally to a medical image diagnosis system.

BACKGROUND

In recent years, a self-propelled X-ray Computed Tomography (CT) apparatus (hereinafter referred to as an "X-ray CT apparatus") has become popular and is used in combination with an X-ray diagnosis apparatus in a surgical scene, etc. A self-propelled X-ray CT apparatus includes a gantry configured to image a subject. The bottom of this gantry is provided with a carrier unit that is moved along a rail disposed on a floor. The self-propelled X-ray CT apparatus can move the gantry to a desired position by moving the carrier unit along the rail.

The top of the rail is provided with a rail cover for preventing the rail from getting soiled with a chemical used in an operation, blood, etc. In the case of moving the gantry along the rail, the carrier unit is moved through a space between the rail and the rail cover. That is, in order to move the carrier unit along the rail, a gap needs to be formed between the rail and the rail cover. On the other hand, since a floor of examination room gets dirty by an operation, etc., a rail is required to have a waterproof property so that the floor can be cleaned by spreading water. However, the existence of a gap between the rail and the rail cover incurs a risk that water enters into the rail through the gap.

BRIEF DESCRIPTION OF THE DRAWINGS

FIG. 2 is a block diagram showing the configuration of the medical image diagnosis system according to the present embodiment.

FIG. 10 is a view showing the carrier unit shown in FIG. 8, when seen from the Z-axis direction.

FIG. 14 is an enlarged view showing a guide roller arranged in a carrying base in a medical image diagnosis system according to a fourth modification.

DETAILED DESCRIPTION

In general, according to one embodiment, a medical image diagnosis system includes a gantry, a rail, an absorbing member and a carrier unit. The rail is disposed on a floor. The rail cover covers the rail. The absorbing member is formed between the floor and the rail cover. The carrier unit is formed in a bottom of the gantry, and is moved along the rail through a space between the rail and the rail cover, and along with movement, attaches and detaches the rail cover with respect to the floor via the absorbing member.

Hereinafter, a medical image diagnosis system according to the present embodiment will be described with reference to the drawings.

Figure 1:
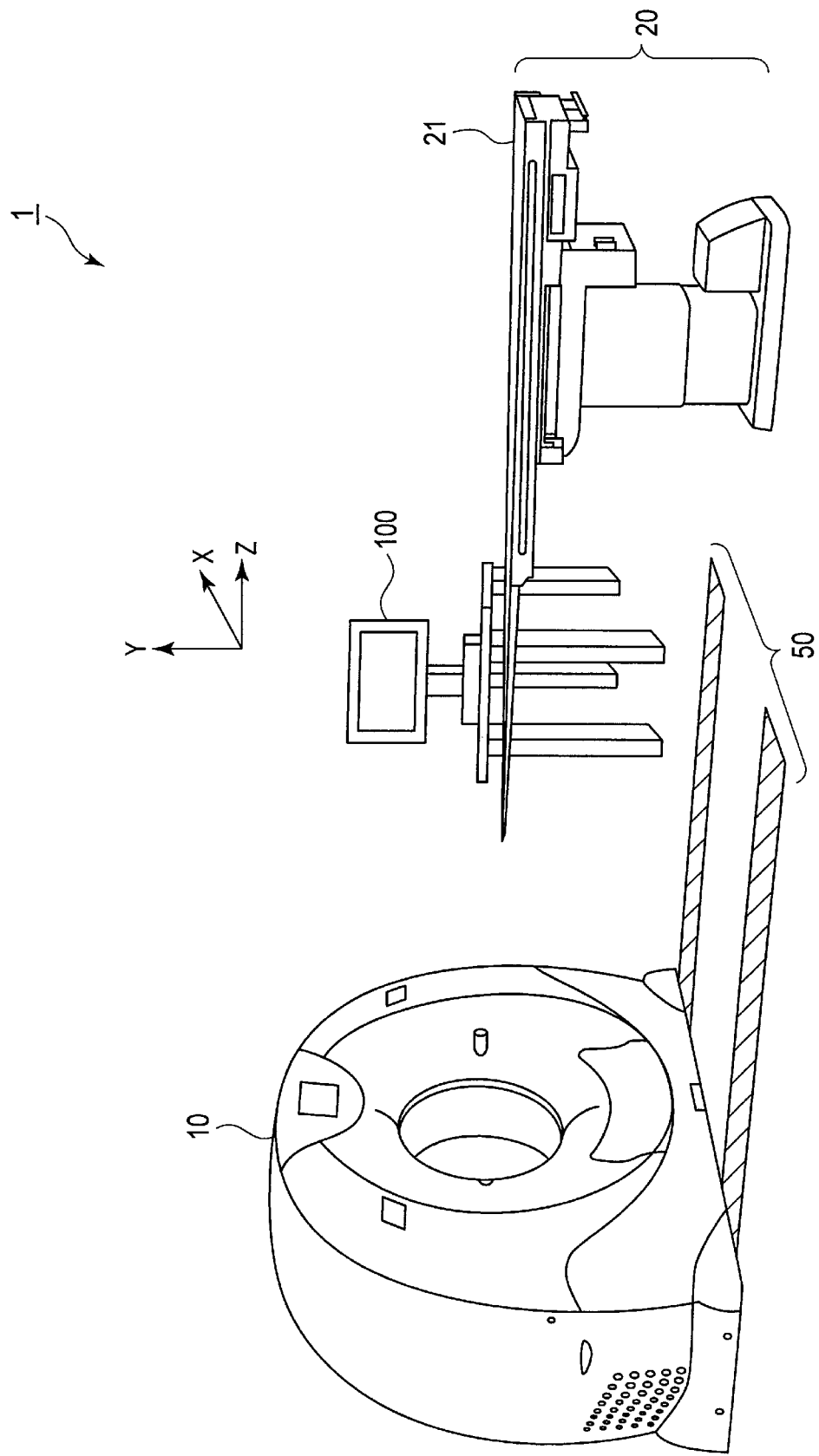
FIG. 1 is a perspective view showing a medical image diagnosis system according to the present embodiment.

FIG. 1 is a perspective view showing a medical image diagnosis system 1 according to the present embodiment. The medical image diagnosis system 1 shown in FIG. 1 includes a medical image diagnosis apparatus and a path 50. The medical image diagnosis apparatus includes, for example, a gantry 10, a console 100, and a bed 20. The following description assumes that a medical image diagnosis apparatus according to the present embodiment is an X-ray CT apparatus. As shown in FIG. 1, an orthogonal coordinate system constituted of the X, Y, and Z axes is defined. That is, the X, Y, Z axes indicate a horizontal direction, a vertical direction, and a moving direction of the gantry 10, respectively. In the orthogonal coordinate system, a direction shown by the arrow is defined as a forward direction.

The gantry 10 is a scanner having a configuration for X-ray CT imaging of a subject. The gantry 10 irradiates a subject with X-rays and acquires projection data from detection data of X-rays transmitted through the subject.

The gantry 10 is provided in an examination room. The console 100 is a computer that controls the gantry 10. The console 100 receives an operator's instruction to the X-ray CT apparatus and reconstructs a CT image from the projection data acquired by the gantry 10. The console 100 is provided in a control room adjacent to the examination room. The gantry 10 and the console 100 are communicatably connected to each other through wire or radio. The bed 20 has a tabletop 21 on which a subject is placed. The path 50 is a movement path for the gantry 10.

In the medical image diagnosis system 1 shown in FIG. 1, for example, the gantry 10 is moved on the path 50 to a position in which a subject placed on the tabletop 21 can be imaged by the gantry 10. The gantry 10 then images a subject placed on the tabletop 21. Next, the gantry 10 is moved on the path 50 to a position away from the bed 20 so as to secure a space for a doctor to perform an operation. A user such as a doctor then specifies a site to operate, by using a medical image imaged by the gantry 10, for example, and operates on the specified site. After the specified site is operated on by the doctor, the operation site is imaged. The gantry 10 is moved on the path 50 again to a position in which a subject placed on the tabletop 21 can be imaged by the gantry 10.

Hereinafter, each configuration of the medical image diagnosis system 1 will be described in detail.

(Configuration of Medical Image Diagnosis System)

FIG. 2 is a block diagram showing the configuration of the medical image diagnosis system 1 according to the present embodiment.

(Description of Gantry)

First, the gantry 10 according to the present embodiment will be described. As shown in FIG. 2, the gantry 10 includes a rotation frame 11, the tabletop 21, an X-ray tube 13, an X-ray detector 15, an X-ray high voltage generator 17, a Data Acquisition System (DAS) 19, an operation panel 27, and a gantry control circuitry 29.

The rotation frame 11 is a housing in an approximately cylindrical shape, in which a bore is formed as an imaging space. The bore substantially corresponds to a Field of View (FOV). As shown in FIG. 2, the X-ray tube 13 and the X-ray detector 15 that are arranged to face each other with the bore interposed therebetween are attached to the rotation frame 11. The rotation frame 11 is a metal frame made, for example, of aluminum, in an annular shape. To be more specific, the gantry 10 includes a main frame (not shown) made of metal such as aluminum. The rotation frame 11 is supported by this main frame via a bearing and the like to be rotatable about a center axis Z.

The rotation frame 11 rotates about the center axis Z at a predetermined angular speed upon receiving power from a rotation actuator 23. Under control of the gantry control circuitry 29, the rotation actuator 23 generates power to rotate the rotation frame 11. The rotation actuator 23 generates power by driving at a rotation speed corresponding to, e.g., a duty ratio of a driving signal from the gantry control circuitry 29. The rotation actuator 23 is implemented by, for example, a motor such as a direct drive motor, a servo motor, etc. The rotation actuator 23 is housed, for example, in the gantry 10.

The tabletop 21 is inserted into the bore of the rotation frame 11. A subject S is placed on the tabletop 21. The tabletop 21 is positioned in a manner so that an imaging target part of the subject S placed on the tabletop 21 is contained in an FOV. The tabletop 21 is supported in a movable manner along the center axis Z of the rotation frame 11. The tabletop 21 is positioned in a manner so that the body axis of the subject S placed on the tabletop 21 corresponds to the center axis Z of the rotation frame 11.

Under control of the console 100 via the gantry control circuitry 29, the X-ray high voltage generator 17 generates a tube voltage to be applied to the X-ray tube 13 and a filament current to be supplied to the X-ray tube 13. As the X-ray high voltage generator 17, an X-ray high voltage generator of any type, such as a variable voltage type, a constant voltage type, a capacitive type, and an inverter type, is applicable. For example, in the case of an inverter type, the X-ray high voltage generator 17 includes an inverter and a high voltage converter. The inverter switches DC from a power circuit at a timing in accordance with control of a tube voltage control circuit, thereby making conversion to an alternating output pulse. The high voltage converter converts the alternating output pulse from the inverter into a DC high voltage.

The X-ray tube 13 is connected to the X-ray high voltage generator 17 via a high voltage cable (not shown). Upon receiving application of a tube voltage and supply of a filament current from the X-ray high voltage generator 17, the X-ray tube 13 generates X-rays so that the subject S placed on the tabletop 21 is irradiated with the X-rays.

The X-ray detector 15 detects X-rays generated by the X-ray tube 13 and transmitted through the subject S. The X-ray detector 15 includes a plurality of X-ray detection elements (not shown) arrayed on a two-dimensional curved surface. Each of the X-ray detection elements detects X-rays from the X-ray tube 13 and converts them into an electrical signal having a peak value according to the intensity of the detected X-rays. Each of the X-ray detection elements includes, for example, a scintillator and a photoelectric converter. Upon receiving X-rays, the scintillator generates fluorescence. The photoelectric converter converts the fluorescence generated by the scintillator into a charge pulse. The charge pulse has a peak value according to the intensity of X-rays. As the photoelectric converter, a circuit element such as a photomultiplier or a photodiode, which converts photons into an electrical signal, is used. The X-ray detector 15 according to the present embodiment is not limited to a detector of an indirect convert type that temporarily converts X-rays into fluorescence and then converts it into an electrical signal, and may be a detector (semiconductor detector) of a direct-convert type that directly converts X-rays into an electrical signal. The X-ray detector 15 is connected to the data acquisition system 19.

The data acquisition system 19 acquires, for each view, digital data representing the intensity of X-rays attenuated by the subject S. The data acquisition system 19 is implemented by, for example, a semiconductor integrated circuitry on which an integrator, an amplifier, and an A/D converter provided in correspondence with each of the plurality of X-ray detection elements are implemented in parallel. The data acquisition system 19 is connected to the X-ray detector 15 within the gantry 10. The integrator integrates electrical signals from an X-ray detection element during a predetermined view period to generate an integral signal. The amplifier amplifies the integral signal output by the integrator. The A/D converter A/D converts the integral signal to generate digital data having a data value corresponding to the peak value of the integral signal. The digital data after conversion is called raw data. Raw data is a set of digital values of X-ray intensity identified by the channel number and the row number of an X-ray detection element as the generation source, and a view number representing an acquired view. The data acquisition system 19 supplies raw data to the console 100 via, for example, a non-contact data transmission circuitry (not shown) housed in the gantry 10.

The operation panel 27 is implemented, for example, by a switch button, a touch pad through which an input operation is carried out by touching an operation surface, and a touch panel display having a display screen and a touch pad integrated as one unit. The operation panel 27 converts an input operation received from an operator into an electrical signal, thereby outputting this signal to the gantry control circuitry 29.

The gantry control circuitry 29 includes, as hardware resources, a processor such as a Central Processing Unit (CPU) or a Micro Processing Unit (MPU), and a memory such as a Read Only Memory (ROM) or a Random Access Memory (RAM). The gantry control circuitry 29 may be implemented by an Application Specific Integrated Circuit (ASIC) or a Field Programmable Gate Array (FPGA), another Complex Programmable Logic Device (CPLD), or a Simple Programmable Logic Device (SPLD). In compliance with the instructions from the console 100, the gantry control circuitry 29 controls the X-ray high voltage generator 17, the data acquisition system 19, and the rotation actuator 23. The processor implements the above function by reading and executing a program stored in the memory.

For example, the gantry control circuitry 29 according to the present embodiment implements a carry function 291 by executing a program. By the carry function 291, the gantry control circuitry 29 moves a carrier unit 25 along a path 50 in accordance with a gantry-moving instruction from an operator via the operation panel 27 or a later-described input circuitry 105. Instead of storing a program on the memory, the program may be directly integrated into the circuitry of the processor. In this case, the processor implements the above function by reading and executing the program integrated into the circuitry.

(Description of Console)

Next, the console 100 according to the present embodiment will be described. The console 100 shown in FIG. 2 includes a processing circuitry 101, a display 103, an input circuitry 105, and a storage 107. Data communication is performed between the processing circuitry 101, the display 103, the input circuitry 105, and the storage 107 via a bus.

The processing circuitry 101 includes, as hardware resources, a processor such as a CPU, an MPU, or a Graphics Processing Unit (GPU), and a memory such as a ROM or a RAM. The processing circuitry 101 executes various programs to implement a preprocessing function 111, a reconstruction function 113, an image processing function 115, and a system control function 117.

By the preprocessing function 111, the processing circuitry 101 performs preprocessing such as logarithmic conversion to raw data transmitted from the gantry 10. The preprocessed raw data is referred to as projection data. By the reconstruction function 113, the processing circuitry 101 generates a CT image representing a space distribution of CT values relating to the subject S based on the projection data generated by the preprocessing function 111. As an image reconstruction algorithm, a known image reconstruction algorithm such as a Filtered Back Projection (FBP) method or a successive approximation reconstruction method may be adopted.

By the image processing function 115, the processing circuitry 101 performs various image processing to the CT image reconstructed by the reconstruction function 113. For example, the processing circuitry 101 generates a display image by performing three-dimensional image processing, such as volume rendering, surface rendering, image value projection processing, Multi-Planer Reconstruction (MPR) processing, Curved MPR (CPR) processing, etc. to the CT image.

By the system control function 117, the processing circuitry 101 comprehensively controls the X-ray CT apparatus according to the present embodiment. Specifically, the processing circuitry 101 reads a control program stored in the storage 107, expands the control program in a memory, and controls the respective units of the X-ray CT apparatus in accordance with the expanded control program.

The preprocessing function 111, the reconstruction function 113, the image processing function 115, and the system control function 117 may be implemented by the processing circuitry 101 on a single substrate, or may be implemented by the processing circuitry 101 on a plurality of substrates.

The display 103 displays various types of data, the aforementioned medial image, etc. Specifically, the display 103 includes a display interface circuitry and a display device. The display interface circuitry converts data representing a display target to a video signal. The video signal is supplied to the display device. The display device displays a video signal representing a display target. For example, a Cathode Ray Tube (CRT) display, a Liquid Crystal Display (LCD), an Organic Electro Luminescence Display (OELD), a plasma display, or any other displays known in this technical field can be appropriately utilized as the display device.

The input circuitry 105 receives various instructions from an operator. Specifically, the input circuitry 105 includes an input device and an input interface circuitry. The input device receives various instructions from a user. As the input device, a trackball, a scroll wheel, a switch button, a mouse, a keyboard, a touch pad through which an input operation is carried out by touching an operation surface, a touch panel display having a display screen and a touch pad integrated as one unit, etc. can be applied. The input interface circuitry supplies an output signal from the input device to the processing circuitry 101 via a bus. In the present embodiment, the input circuitry 105 is not limited to a circuitry that includes physical operation components such as a trackball, a scroll wheel, a switch button, a mouse, a keyboard, etc. Examples of the input circuitry 105 include a processing circuitry that receives an electrical signal corresponding to an input operation through an external input device provided separately from the apparatus, and outputs the electrical signal to the processing circuitry 101.

The storage 107 is a storage device such as a Hard Disk Drive (HDD), a Solid State Drive (SSD), or an integrated circuit storage device, which stores various types of information. Other than HDD, SSD, etc., the storage 107 may be a driving device that reads and writes various types of information to and from a portable storage medium such as a Compact Disc (CD), a Digital Versatile Disc (DVD), a flash memory, etc. The storage 107 may have its storage area within the X-ray CT apparatus or a network-connected external storage device. For example, the storage 107 stores data on a CT image or a display image. The storage 107 further stores, e.g., a control program according to the present embodiment.

(Description of Carrier Unit)

Next, the carrier unit 25 according to the present embodiment will be described. The carrier unit 25 is provided, for example, in the bottom of the gantry 10. The carrier unit 25 is, for example, a wagon that is moved along the path 50 under control of the gantry control circuitry 29. By moving the carrier unit 25 along the path 50, the gantry 10 can be moved to a desired position.

Described below are the carrier unit 25 according to the present embodiment and the configuration of the path 50 on which the carrier unit 25 is moved.

(Configuration of Path)

Figure 3:
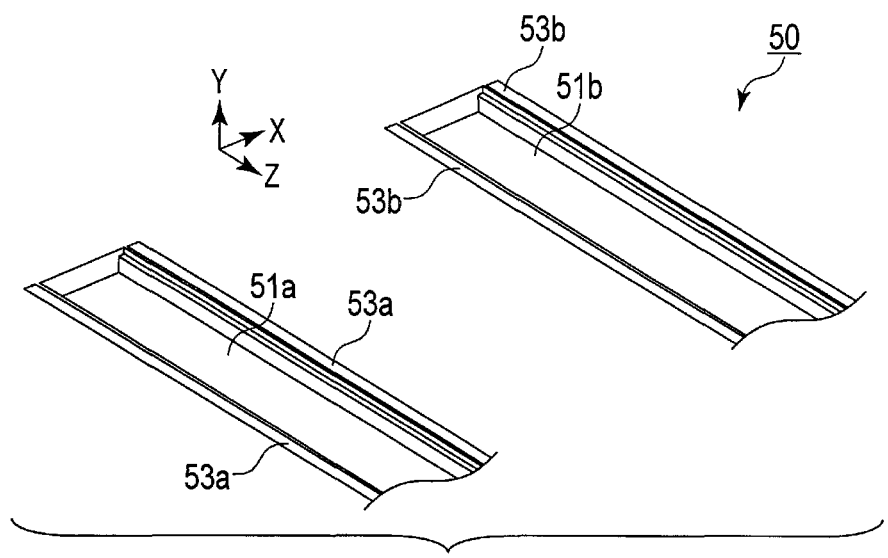
FIG. 3 is a view showing the appearance of rails formed in a path shown in FIG. 1.
Figure 4:
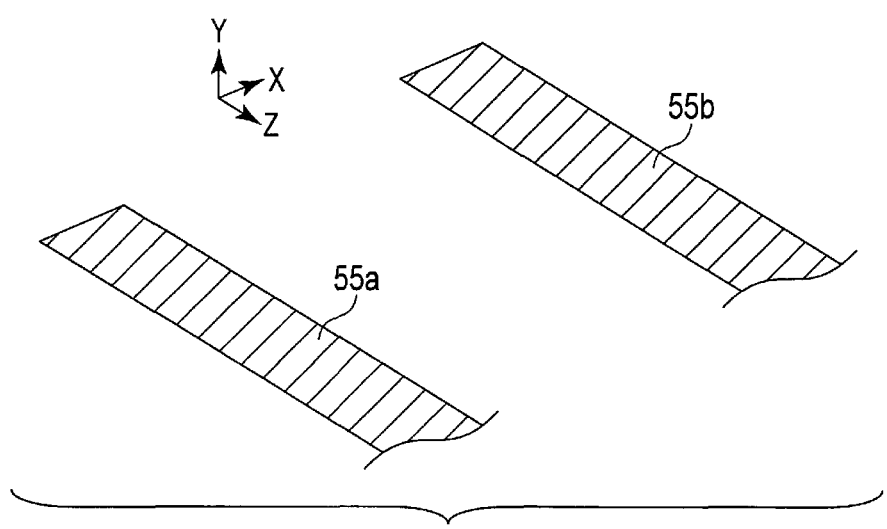
FIG. 4 is a view showing the appearance of rail covers that cover the rails shown in FIG. 3.
Figure 5:
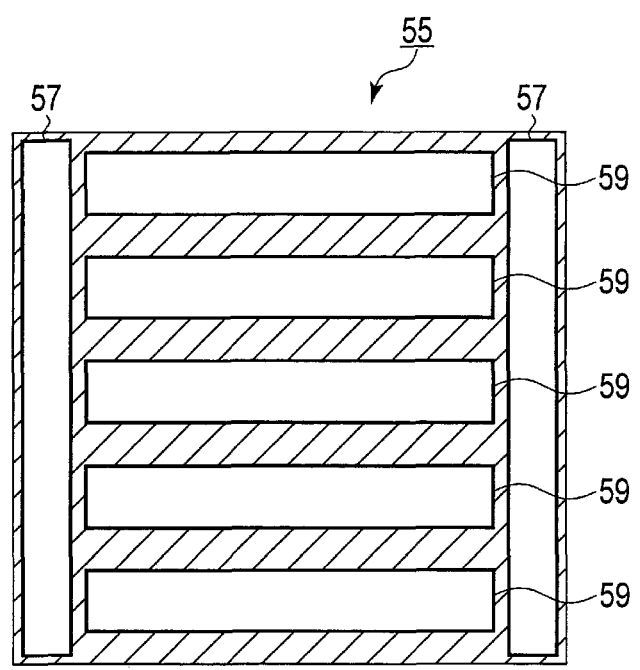
FIG. 5 is a view showing the configuration of a rear face of each of the rail covers shown in FIG. 4.

FIG. 3 is a view showing the appearance of rails 51a and 51b formed in the path 50 shown in FIG. 1. FIG. 4 is a view showing the appearance of rail covers 55a and 55b that cover the rails 51a and 51b shown in FIG. 3. FIG. 5 is a view showing the configuration of a rear face of each of the rail covers 55a and 55b shown in FIG. 4.

As shown in FIG. 3, the rails 51a and 51b are disposed on the bottoms of the grooves formed in a floor. The rails 51a and 51b are carrying paths for carrying the gantry 10. The rail 51a is a carrying path on the right in the moving direction of the gantry 10. The rail 51b is a carrying path on the left in the moving direction of the gantry 10. The rails 51a and 51b are made of a material that allows a carrying base 60 to run. For example, the rails 51a and 51b are formed by processing a material in a sheet form that can be disposed in the grooves. In addition, metallic members 53a and 53b are buried in the floor along the longitudinal direction of the rails 51a and 51b. These metallic members 53a and 53b may be buried in a part of the floor, or in the floor so as to surround the rails 51a and 51b.

As shown in FIG. 4, the rail 51a and the metallic member 53a are covered with the rail cover 55a. The rail 51b and the metallic member 53b are covered with the rail cover 55b. The rail covers 55a and 55b are formed in a manner to prevent a liquid such as a chemical used in an operation, blood, water spread for cleaning, etc. from entering into the rails 51a and 51b. The rail covers 55a and 55b are made of a material such as polyurethane, for example.

In the case where rear surfaces of the rail covers 55a and 55b are defined as those close to the rails 51a and 51b, a magnetic member 57 in a sheet form is mounted as an absorbing member on the rear surfaces of the rail covers 55a and 55b, as shown in FIG. 5. The magnetic member 57 is mounted along both ends in the longitudinal direction of each of the rail covers 55a and 55b. In the case of the rail covers 55a and 55b coming in contact with the floor, the magnetic member 57 comes in tight magnetic contact with no gap with the metallic members 53a and 53b formed in the floor. By this tight magnetic contact with the metallic members 53a and 53b with no gap, the magnetic member 57 fills gaps generated between the rail 51a and the rail cover 55a and between the rail 51b and the rail cover 55b. This prevents a liquid such as a chemical, blood, water, etc. from entering into the rails 51a and 51b. On the rear surface of each of the rail covers 55a and 55b, a reinforcing board (for example, a rib for reinforcement) 59 for securing the strength of the rail covers 55a and 55b is mounted.

Hereinafter, the rails 51a and 51b are collectively referred to as a rail 51 if no distinction is made therebetween. Similarly, the metallic members 53a and 53b are collectively referred to as a metallic member 53 if no distinction is made therebetween. In addition, the rail covers 55a and 55b are collectively referred to as a rail cover 55 if no distinction is made therebetween.

(Configuration of Carrier Unit)

Figure 6:
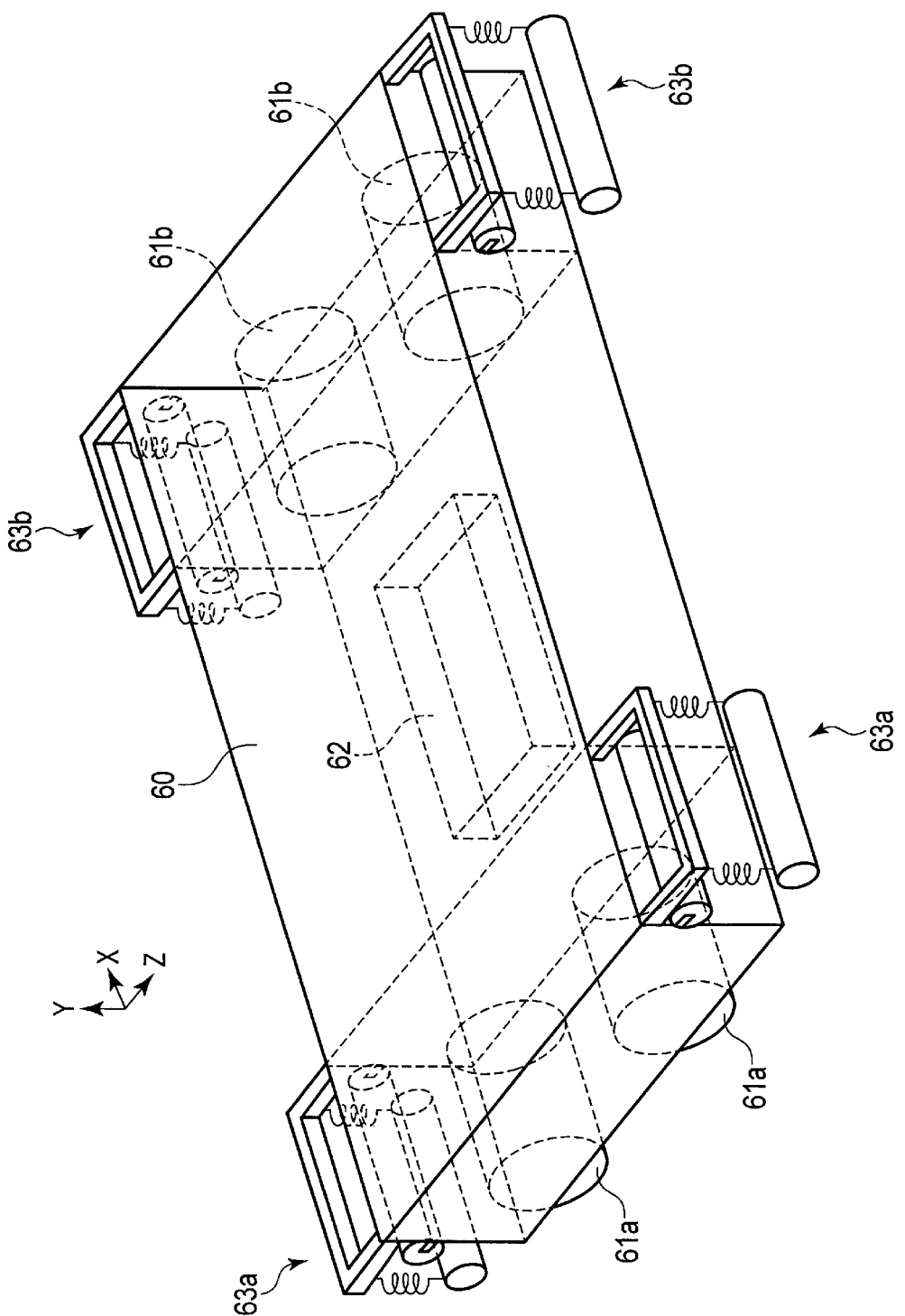
FIG. 6 is a perspective view showing the configuration of the carrier unit shown in FIG. 2.

FIG. 6 is a perspective view showing the configuration of the carrier unit 25 shown in FIG. 2. As shown in FIG. 6, the carrier unit 25 includes the carrying base 60. The carrying base 60 is, for example, a housing on which the gantry 10 can be installed. The carrying base 60 is provided in the bottom of the gantry 10 and is moved along the rails 51a and 51b. In the case where the gantry 10 is moved along the rails 51a and 51b, the carrying base 60 is moved through spaces between the rail 51a and the rail cover 55a and between the rail 51b and the rail cover 55b. That is, the carrying base 60 is moved under the rail covers 55a and 55b.

The carrying base 60 includes wheels 61a and 61b, a carrying actuator 62, and guide rollers 63a and 63b. The wheels 61a and 61b are provided in the bottom of the carrying base 60. The wheel 61a is formed in a position corresponding to the rail 51a. The wheel 61b is formed in a position corresponding to the rail 51b.

The carrying actuator 62 generates power to move the carrying base 60 along the rails 51a and 51b. The carrying actuator 62 drives at a rotation speed corresponding to, e.g., a duty ratio of a driving signal from the gantry control circuitry 29, thereby rotating the wheels 61a and 61b connected to the carrying actuator 62. The carrying actuator 62 is implemented by a motor such as a direct drive motor or a servo motor. The carrying actuator 62 is housed, for example, in the carrying base 60.

Guide rollers 63a and 63b are arranged, for example, in the four corners of the carrying base 60. Along with the movement of the carrying base 60, the guide rollers 63a and 63b guide the rail covers 55a and 55b from the tops of the rails 51a and 51b to the top of the carrying base 60. Furthermore, as the carrying base 60 is moved, the guide rollers 63a and 63b guide the rail covers 55a and 55b from the top of the carrying base 60 to the tops of the rails 51a and 51b.

Figure 7:
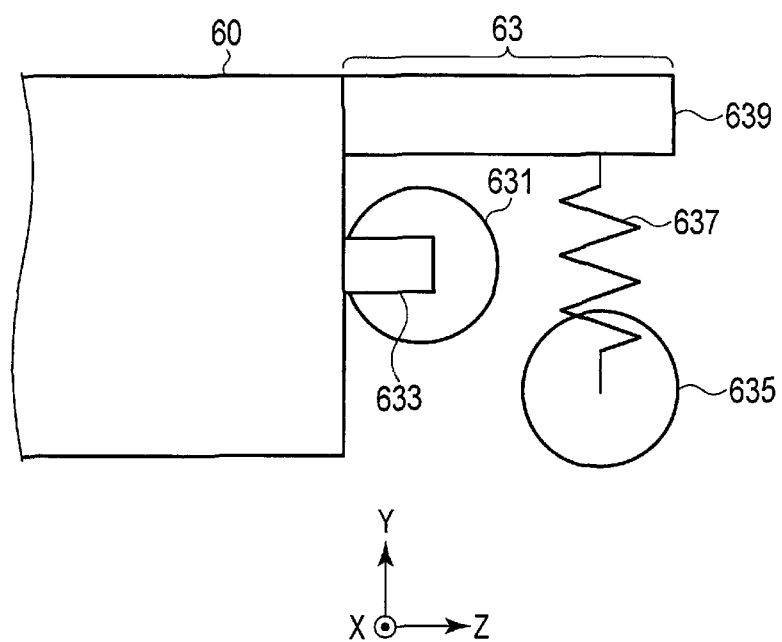
FIG. 7 is an enlarged view showing a guide roller arranged in a carrying base shown in FIG. 6.

FIG. 7 is an enlarged view showing guide rollers 63a and 63b arranged in the carrying base 60 shown in FIG. 6. Hereinafter, the guide rollers 63a and 63b are collectively referred to as a guide roller 63 if no distinction is made therebetween. The guide roller 63 includes a first roller unit and a second roller unit.

In the case where the carrying base 60 is moved along the rail 51, the first roller unit lifts the rail cover 55 from the top of the rail 51 to the top of the carrying base 60. The first roller unit is arranged in the moving direction side of the carrier unit 25. The first roller unit includes a first roller 631 and a first roller supporting member 633.

The first roller 631 has an approximately cylindrical shape and is a structure that is supported in a manner to be rotatable about a predetermined rotation axis. In the case where the carrying base 60 is moved along the rail 51, the first roller 631 lifts the rail cover 55 from the top of the rail 51 to the top of the carrying base 60. A first roller supporting member 633 supports the first roller 631 with respect to the carrying base 60.

In the case where the carrying base 60 is moved along the rail 51, the second roller unit pushes down the rail cover 55 that has been lifted to the top of the carrying base 60, from the top of the carrying base 60 to the top of the rail 51. The second roller unit is arranged in the reverse side to the moving direction of the carrier unit 25. The second roller unit includes a second roller 635 and a push-down unit.

Similar to the first roller 631, the second roller 635 has an approximately cylindrical shape and is a structure that is supported in a manner to be rotatable about a predetermined rotation axis. In the case where the carrying base 60 is moved along the rail 51, the second roller 635 pushes down the rail cover 55 that the first roller 631 has lifted to the top of the carrying base 60, from the top of the carrying base 60 to the top of the rail 51.

The push-down unit is to push down the rail cover 55 lifted to the top of the carrying base 60, to the floor with the aid of a member having elasticity. The push-down unit includes an elastic member 637 and a second roller supporting member 639. The elastic member 637 pushes down to the floor, the rail cover 55 that is attached to the second roller 635 and has been lifted by the first roller 631 to the top of the carrying base 60. The elastic member 637 is, for example, a spring or a suspension. The second roller supporting member 639 supports the elastic member 637 with respect to the carrying base 60.

(Configuration of Carrier Unit provided in Path)

Figure 8:
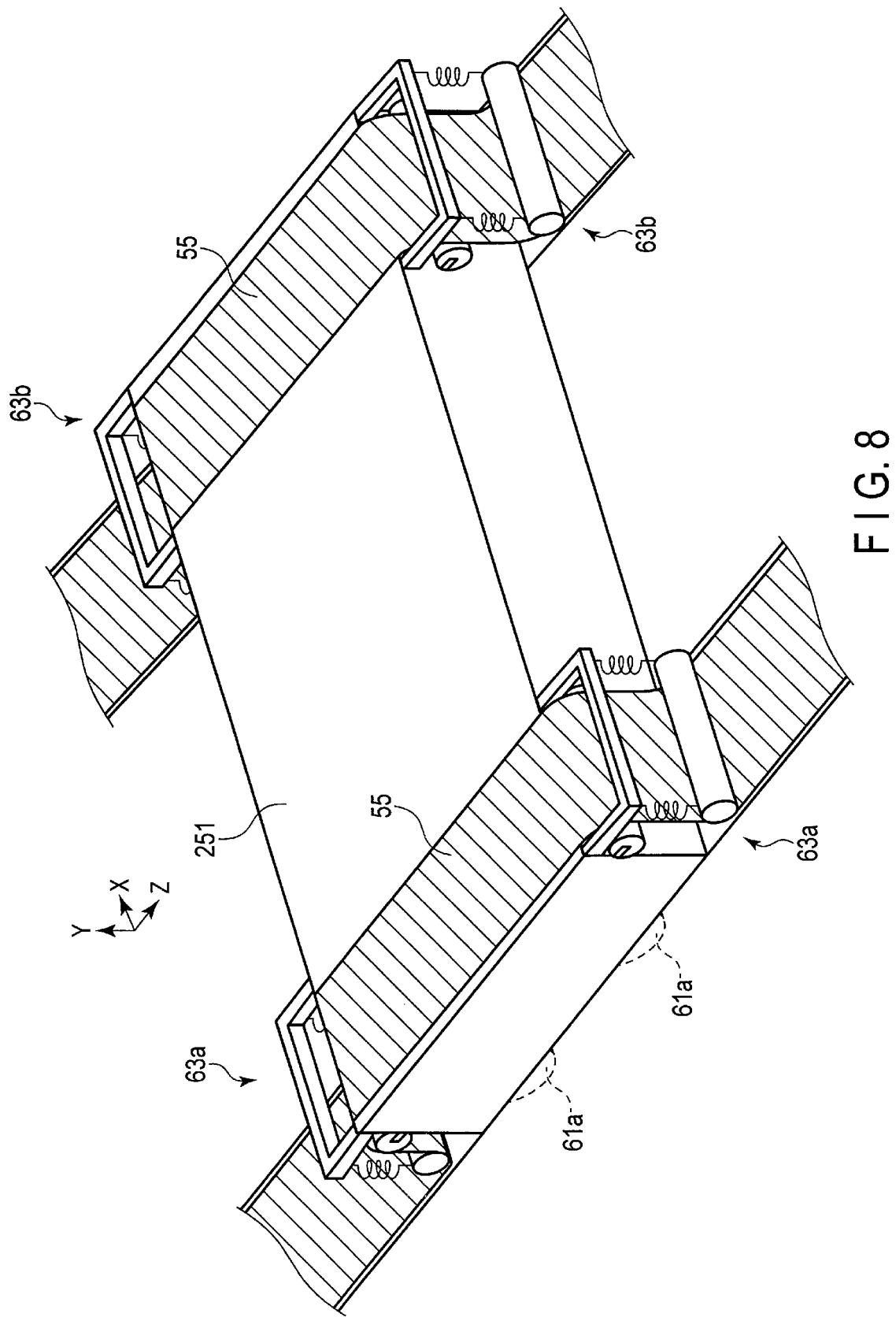
FIG. 8 is a perspective view showing the carrier unit provided in the path shown in FIG. 3.
Figure 9:
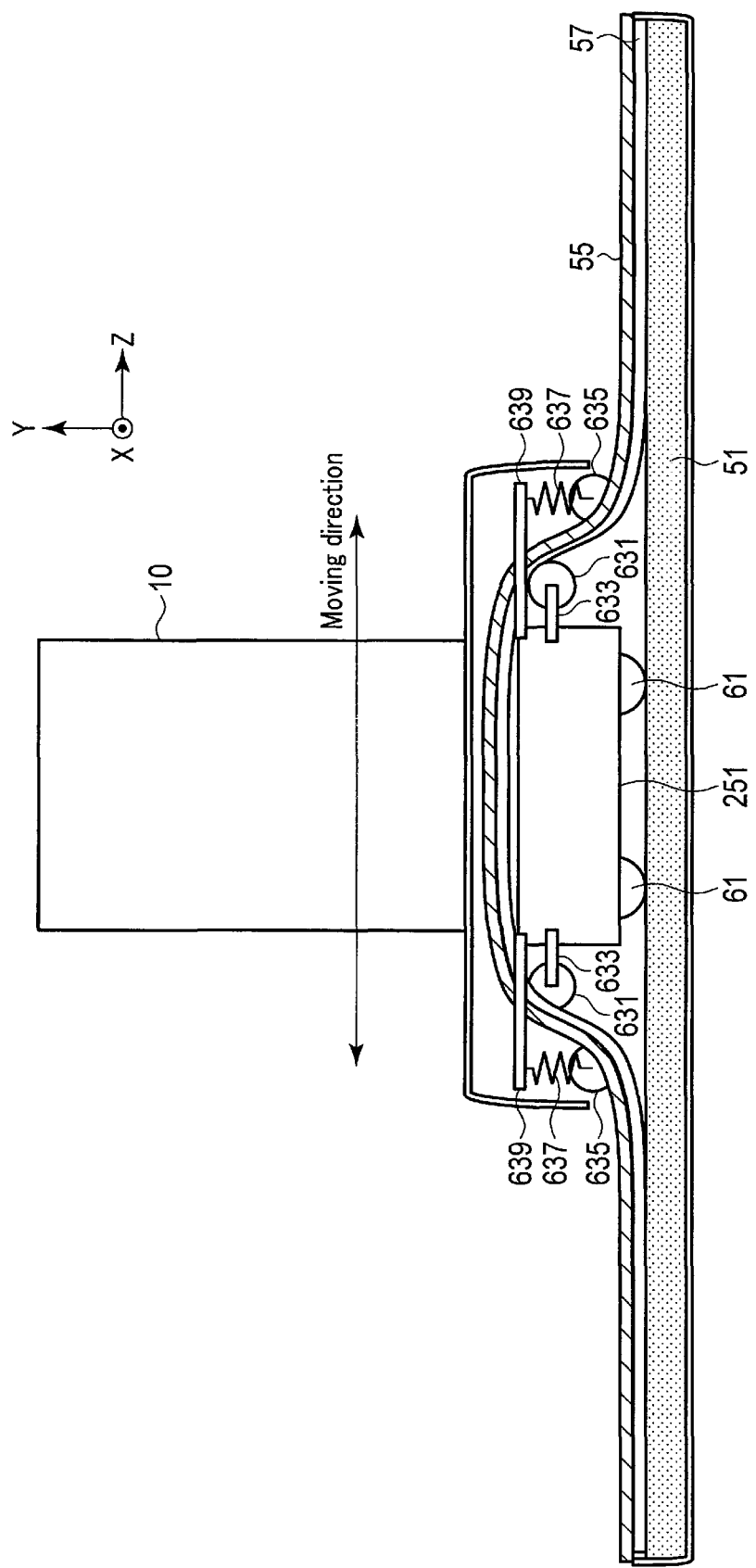
FIG. 9 is a view showing the carrier unit shown in FIG. 8, when seen from the X-axis direction.

FIG. 8 is a perspective view showing the carrier unit 25 provided in the path 50 shown in FIG. 3. FIG. 9 is a view showing the carrier unit 25 shown in FIG. 8, when seen from the X-axis direction. FIG. 10 is a view showing the carrier unit 25 shown in FIG. 8, when seen from the Z-axis direction. Herein, the movement of the rail cover 55 in the case where the carrier unit 25 is moved along the path 50 will be explained with reference to FIGS. 8 to 10. For example, the movement is explained based on the assumption that the carrier unit 25 is moved along the path 50 in the forward direction of the Z-axis. The forward direction of the Z-axis is the direction indicated by the arrow of the Z-axis shown in each of FIGS. 8 to 10.

As shown in FIGS. 8 to 10, the magnetic member 57 formed in the rail cover 55 brings the rail cover 55 that is in contact with a floor, in tight magnetic contact with no gap with the metallic member 53 arranged in the floor. This prevents entry of a liquid into the rails 51a and 51b.

Next, the rail cover 55 in contact with the floor is pulled in the first roller 631 and the second roller 635 arranged on the moving direction side of the carrying base 60, as the carrying base 60 is moved. The rail cover 55 that the magnetic member 57 brings in tight contact with the floor with no gap left is pulled away from the floor and is lifted by the first roller 631 from the top of the rail 51 to the top of the carrying base 60.

Next, the rail cover 55 lifted to the top of the carrying base 60 is moved on the carrying base 60 as the carrying base 60 is moved. In addition, the rail cover 55 lifted to the top of the carrying base 60 is pulled in the first roller 631 and the second roller 635 arranged on the reverse side to the moving direction of the carrying base 60. The rail cover 55 lifted to the top of the carrying base 60 is pushed down by the second roller 635, from the top of the carrying base 60 to the top of the rail 51.

Lastly, the rail cover 55 that has been pushed down from the top of the carrying base 60 to the top of the rail 51 is pushed against the floor by the elastic member 637 formed on the reverse side to the moving direction. In this manner, the magnetic member 57 formed in the rail cover 55 can be brought in tight magnetic contact again with the metallic member 53 formed in the floor, with no gap. Accordingly, entry of a liquid into the rails 51a and 51b can be prevented.

With the configuration described above, the medical image diagnosis system 1 according to the present embodiment is provided with the magnetic member 57 between the rail 51 and the rail cover 55. In a portion where the rail cover 55 is in contact with the floor, the magnetic member 57 is in tight contact with the metallic member 53 formed in the floor, with no gap left. The rail 51 and the rail cover 55 are made smooth by the second roller 635 arranged in each of the front and the rear of the carrying base 60 so that the rail 51 and the rail cover 55 can come in tight contact with each other with no gap left. Due to the formation of the elastic member 637 in the second roller 635, even in the case of the rail 51 having an uneven surface, the magnetic member 57 can be brought in tight magnetic contact with no gap with the metallic member 53 formed in the floor, by constantly applying a pressure of a certain level or more to the rail cover 55. This allows the medical image diagnosis system 1 according to the present embodiment to provide the rail 51 with a waterproof property so that a floor of an examination room can be easily cleaned.

(First Modification)

In the medical image diagnosis system 1 according to the above embodiment, in order to attach and detach the rail cover 55 with respect to a floor along with the movement of the gantry 10, the magnetic member 57 is attached to the rail cover 55, in which the magnetic member 57 is shaped in a sheet form and is brought in tight magnetic contact with no gap with the metallic member 53 formed in the floor. However, the medical image diagnosis system 1 according to the present embodiment is not limited to this configuration. In the medical image diagnosis system 1 according to the above embodiment, in order to attach and detach the rail cover 55 with respect to a floor along with the movement of the gantry 10, a deformable member 65 may be attached to the rail cover 55, in which the deformable member 65 fits in a groove that is formed in the floor in a manner to extend along the rail 51.

Figure 11:
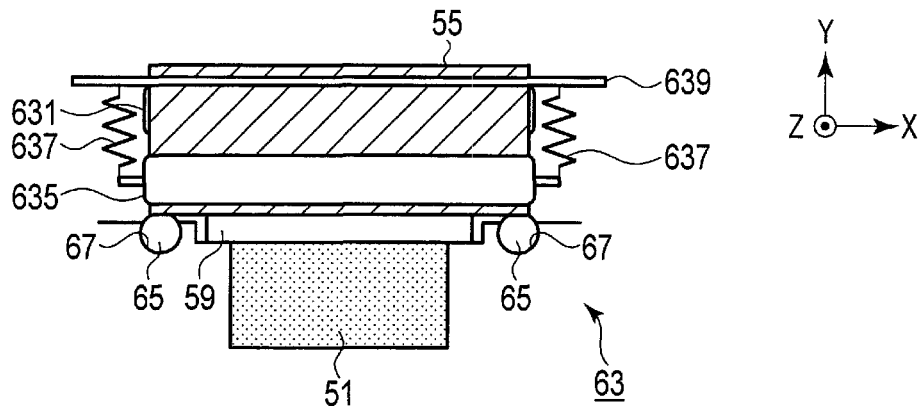
FIG. 11 is a view showing a carrier unit when seen from the Z-axis direction in a medical image diagnosis system according to a first modification.

FIG. 11 is a view showing the carrier unit 25 when seen from the Z-axis direction in the medical image diagnosis system 1 according to the first modification. FIG. 11 is an enlarged view of one of guide rollers 63 of the carrier unit 25 when seen from the Z-axis direction. As shown in FIG. 11, instead of the magnetic member 57, the deformable member 65 is mounted along each end in the longitudinal direction of the rail cover 55. The deformable member 65 is rubber or resin. As shown in FIG. 11, a groove 67 is formed in the floor. A part of the rail cover 55, in which the carrier unit 25 is positioned, is pushed against the floor by the elastic member 637 formed on the reverse side to the moving direction. By pushing the rail cover 55 against the floor, the deformable member 65 formed in the rail cover 55 is deformed to fit with no gap in the groove 67 formed in the floor. This allows the medical image diagnosis system 1 according to the first modification to provide the rail 51 with a waterproof property so that a floor of an examination room can be easily cleaned.

(Second Modification)

In the medical image diagnosis system 1 according to the above embodiment, in order to attach and detach the rail cover 55 with respect to a floor along with the movement of the gantry 10, the magnetic member 57 is attached to the rail cover 55, in which the magnetic member 57 is shaped in a sheet form and is brought in tight magnetic contact with no gap with the metallic member 53 formed in the floor. In the medical image diagnosis system 1 according to the first modification, in order to attach and detach the rail cover 55 with respect to a floor along with the movement of the gantry 10, the deformable member 65 is attached to the rail cover 55, in which the deformable member 65 fits with no gap in the groove that is formed in the floor in a manner to extend along the rail 51. However, the medical image diagnosis system 1 according to the present embodiment is not limited to this configuration. In the medical image diagnosis system 1 according to the present embodiment, for example, a hook-and-loop fastener may be mounted between a floor and the rail cover 55 in order to attach and detach the rail cover 55 with respect to the floor along with the movement of the gantry 10.

Figure 12:
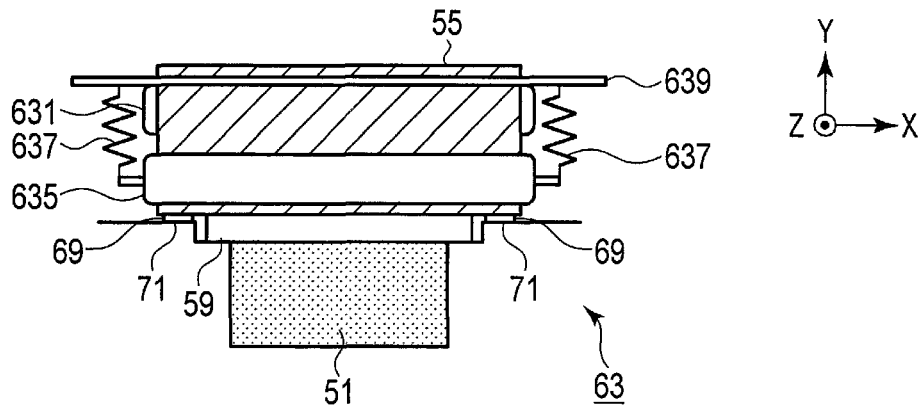
FIG. 12 is a view showing a carrier unit when seen from the Z-axis direction in a medical image diagnosis system according to a second modification.

FIG. 12 is a view showing the carrier unit 25 when seen from the Z-axis direction in the medical image diagnosis system 1 according to the second modification. Similar to FIG. 11, FIG. 12 is an enlarged view of one of guide rollers 63 of the carrier unit 25 when seen from the Z-axis direction. As shown in FIG. 12, instead of the magnetic member 57 or the deformable member 65, a hook-and-loop fastener is mounted between a floor and the rail cover 55 along each end in the longitudinal direction of the rail cover 55. The hook-and-loop fastener includes a loop 69 and a hook 71. For example, instead of the magnetic member 57 or the deformable member 65, the loop 69 is mounted along each end in the longitudinal direction of the rail cover 55. The hook 71 is formed in a floor in a manner to extend along the rail 51. A part of the rail cover 55, in which the carrier unit 25 is positioned, is pushed against the floor by the elastic member 637 formed on the reverse side to the moving direction. By pushing the rail cover 55 against the floor, the loop 69 formed in the rail cover 55 and the hook 71 formed in the floor are brought in tight contact with each other with no gap left. This allows the medical image diagnosis system 1 according to the second modification to provide the rail 51 with a waterproof property, so that a floor of an examination room can be easily cleaned.

(Third Modification)

In the medical image diagnosis system 1 according the above embodiment, the second roller 635 having a width substantially corresponding to a width in the X-axis direction of the rail cover 55 is mounted on the carrying base 60 with the elastic member 637 and the second roller supporting member 639 interposed between the second roller 635 and the carrying base 60. However, the medical image diagnosis system 1 according to the present embodiment is not limited to this configuration. In the medical image diagnosis system 1 according the above embodiment, for example, a plurality of mini-rollers 73 may be mounted.

Figure 13:
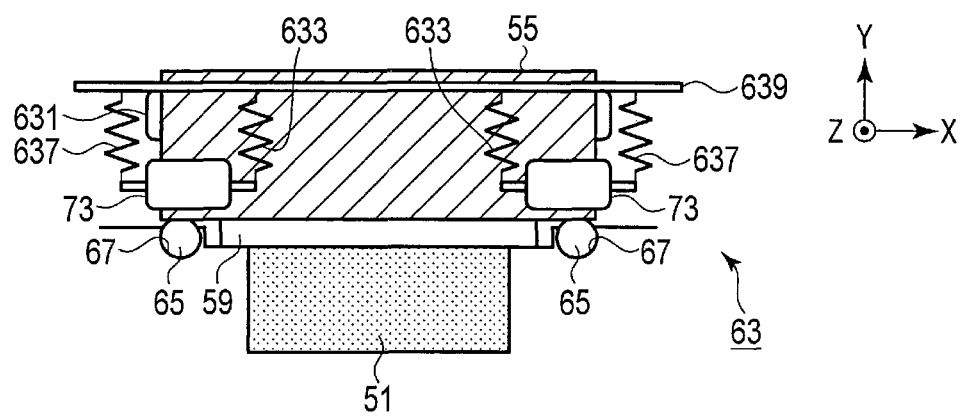
FIG. 13 is a view showing a carrier unit when seen from the Z-axis direction in a medical image diagnosis system according to a third modification.

FIG. 13 is a view showing the carrier unit 25 when seen from the Z-axis direction in the medical image diagnosis system 1 according to the third modification. Similar to FIGS. 11 and 12, FIG. 13 is an enlarged view of one of guide rollers 63 of the carrier unit 25 when seen from the Z-axis direction. As shown in FIG. 12, the plurality of mini-rollers 73 may be formed in a manner to match the position of the deformable member 65 mounted along each end in the longitudinal direction of the rail cover 55 and the position of the groove 67 formed in the floor along the rail 51.

(Fourth Modification)

In the medical image diagnosis system according to the above embodiment, in the case of moving the carrying base 60 along the rail 51, a part of the rail cover 55, in which the carrier unit 25 is positioned, is lifted by the first roller 631 formed on the moving direction side, from the top of the rail 51 to the top of the carrying base 60. Accordingly, in the case of moving the carrying base 60 along the rail 51, a gap is temporarily generated between the rail 51 and the rail cover 55. With a liquid such as a chemical, blood, water, etc. being attached on the rail cover 55, in the case of lifting up this rail cover 55 by the first roller 631, there is a risk that the liquid such as a chemical, blood, water, etc. enters into the rail 51 through the gap.

FIG. 14 is an enlarged view showing the guide roller 63 formed in the carrying base 60 of a medical image diagnosis system 1 according to the fourth modification. As shown in FIG. 14, in the medical image diagnosis system 1 according to the fourth modification, a removable mechanism 641 configured to remove a liquid attached on the rail cover 55 is mounted to the carrying base 60 by the supporting member 643. For example, a sponge is attached as the removable mechanism 641. The removal mechanism 641 is attached on the moving direction side of the carrying base 60. Due to the removal mechanism 641 removing a liquid attached on the rail cover 55, the liquid attached on the rail cover 55 can be prevented from entering into the rail 51 through the gap temporarily generated.

As described above, the medical image diagnosis system according to the present embodiment comprises a gantry; a rail disposed on a floor; a rail cover that covers the rail; an absorbing member formed between the floor and the rail cover; a carrier unit that is formed in a bottom of the gantry, is moved along the rail through a space between the rail and the rail cover, and along with movement, attaches and detaches the rail cover with respect to the floor via the absorbing member.

With the above configuration, in the medical image diagnosis system according to the present embodiment, the rail cover can be brought in tight contact with no gap with a floor by forming the absorbing member between the rail and the rail cover. This allows the medical image diagnosis system according to the embodiment to provide the rail with a waterproof property, so that a floor of an examination room can be easily cleaned.

Accordingly, the medical image diagnosis system according to the present embodiment can improve the cleaning efficiency of an examination room.

The embodiment described above assumes that the medical image diagnosis apparatus is an X-ray CT apparatus. However, the present embodiment is not limited to this. The present embodiment is applicable in a similar manner to, for example, a Magnetic Resonance Imaging (MRI) apparatus, a Single Photon Emission Computed Tomography (SPECT) apparatus, a Positron Emission computed Tomography (PET) apparatus, an SPECT-CT apparatus having an SPECT apparatus and an X-ray CT apparatus integrated as one unit, a PET-CT apparatus having a PET apparatus and an X-ray CT apparatus integrated as one unit, or a PET-MRI apparatus having a PET apparatus and an MRI apparatus integrated as one unit.

Described in the above embodiment is a case where the number of rails 51 is two. However, the present embodiment is not limited to this case. For example, the number of rails 51 may be one or three or more.

Furthermore, the above embodiment described the medical image diagnosis system 1 having a self-propelled medical image diagnosis apparatus; however, the present embodiment is not limited to this. For example, the carrying base 60 to which a wheel 61 is mounted may be manually moved on the rail 51. Alternatively, a manually-movable mechanism may be provided in combination with a self-propelled mechanism.

The term "processor" used in the above explanation means, for example, an exclusive or general processor, a circuit (circuitry), a processing circuit (circuitry), an operation circuit (circuitry), an arithmetic circuit (circuitry), or a circuitry such as an Application Specific Integrated Circuit (ASIC) or a programmable logic device (for example, an Simple Programmable Logic Device (SPLD), a Complex Programmable Logic Device (CPLD), or a Field Programmable Gate Array (FPGA)). In addition, each component (each processing unit) according to the present embodiment may be implemented by not only a single processor, but also a plurality of processors. Furthermore, a plurality of components (a plurality of processing units) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis system comprising:
   a gantry;
   a rail disposed on a floor;
   a rail cover that covers the rail;
   an absorbing member formed between the floor and the rail cover; and
   a carrier unit that is formed in a bottom of the gantry, is moved along the rail through a space between the rail and the rail cover, and along with movement, attaches and detaches the rail cover with respect to the floor via the absorbing member.

2. The system according to claim 1, wherein the carrier unit includes:
   a base on which the gantry is mounted; and
   a wheel that is provided in a bottom of the base to move the base along the rail.

3. The system according to claim 2, wherein the carrier unit further includes:

a first roller that, in a case of moving the base along the rail, lifts the rail cover from a top of the rail to a top of the base; and a second roller that, in a case of moving the base along the rail, pushes down the lifted rail cover from the top of the base to the top of the rail.

4. The system according to claim 3, wherein the first roller is arranged on a moving direction of the carrier unit, the second roller is arranged on a reverse side to the moving direction of the carrier unit.

5. The system according to claim 3, wherein the second roller includes a push-down unit that pushes the lifted rail cover against the floor.

6. The system according to claim 5, wherein the push-down unit includes:

an elastic member that pushes the lifted rail cover against the floor; and a supporting member that supports the elastic member with respect to the base.

7. The system according to claim 6, wherein the elastic member is a spring or a suspension.

8. The system according to claim 1, wherein the absorbing member includes a magnetic member that comes in tight magnetic contact with no gap with a metallic member disposed on the floor.

9. The system according to claim 1, wherein the absorbing member includes a deformable member that fits with no gap in a groove formed in the floor in a manner to extend along the rail.

10. The system according to claim 9, wherein the deformable member is rubber or resin.

11. The system according to claim 1, wherein the absorbing member is a hook-and-loop fastener.

* * * * *